United States Patent [19]

Gabetta et al.

[11] Patent Number: 4,764,508
[45] Date of Patent: Aug. 16, 1988

[54] COMPLEXES OF FLAVANOLIGNANS WITH PHOSPHOLIPIDS, PREPARATION THEREOF AND ASSOCIATED PHARMACEUTICAL COMPOSITIONS

[75] Inventors: Bruno Gabetta; Ezio Bombardelli; Giorgio Pifferi, all of Milan, Italy

[73] Assignee: Inverni Della Beffa S.p.A., Milan, Italy

[21] Appl. No.: 882,608

[22] Filed: Jul. 7, 1986

[30] Foreign Application Priority Data

Jul. 17, 1985 [IT] Italy ................ 21602 A/85

[51] Int. Cl.$^4$ ................ A61K 31/685; C07D 311/32; C07D 311/00; C07D 319/20
[52] U.S. Cl. ................ 514/78; 549/400; 549/362; 549/289
[58] Field of Search ............ 549/362, 400, 220, 289; 514/452, 78

[56] References Cited

U.S. PATENT DOCUMENTS 4,358,442 11/1982 Wirte-Peitz et al. ........... 514/78

FOREIGN PATENT DOCUMENTS 1963318 6/1971 Fed. Rep. of Germany ...... 514/452

*Primary Examiner*—Nicky Chan
*Attorney, Agent, or Firm*—Bucknam and Archer

[57] ABSTRACT

The invention relates to novel compounds comprising lipophilic complexes of silybin, silidianin, and silicristin with phospholipids, and the preparation of these complexes by non-conventional methods. Absorption of the novel compounds in the gastrointestinal tract is appreciably greater, resulting in higher plasma levels than for the individual flavanolignans. The resulting improvement in the pharmacokinetic and pharmacological parameters is such that the substances can advantageously be used in the treatment of acute and chronic liver disease of toxic, metabolic or infective origin or of degenerative nature.

8 Claims, No Drawings

COMPLEXES OF FLAVANOLIGNANS WITH PHOSPHOLIPIDS, PREPARATION THEREOF AND ASSOCIATED PHARMACEUTICAL COMPOSITIONS

The invention relates to novel complexes of phospholipids with the main constituents of silymarin, a known standardized extract obtained from seeds of Silybum marianum and used in the treatment of liver disease of varying origin. Silymarin contains three main constituents: silybin, silidianin and silicristin, which are assumed to be responsible for the therapeutic liver-protecting activity of the extract. The main constituent is silybin, which is a mixture of two diasteroisomers (Chem. Commun. 696, 1979) in the ratio of about 1:1, for which the largest amount of pharmaco-toxicological and clinical documentation exists, with regard to the hydrosoluble hemisuccinic diester.

The activity of silybin and the other constituents of silymarin, particularly when administered by injection, occurs at the liver cell, where the flavanolignans intervene in the process of stabilizing and protecting the liver-cell membrane against injurious agents such as carbon tetrachloride, phalloidine, amanitine, some heavy metals, galactosamine and various antibiotics which interfere with its function by liberating enzymes resulting in the formation of necrosis. Some of these injurious agents simulate the damage produced by viruses responsible for common forms of hepatitis in man—hence the therapeutic importance of antihepatotoxic molecules of this kind. As the reported data in the literature show, the best protection against the aforementioned injurious agents is obtained in the animal when the compounds are administered intraperitoneally or intravenously so as rapidly to obtain high concentrations in the bloodstream and the target organ. In spite of occasional reports of oral absorption of silybin (Arzneim. Forsch. 23, 1322, 1973; Arzneim. Forsch. 25, 902, 1975; Planta Medica 45, 216, 1982), the relevant pharmacological investigations are scanty and difficult to reproduce. This indicates that the drug does not have really high or adequate bioavailability when administered by this method.

The invention relates to the production of novel compounds obtained by chemical interaction between one or more phospholipids and one or more of the aforementioned flavanolignans.

The compounds according to the invention are characterized by the general formula (I):

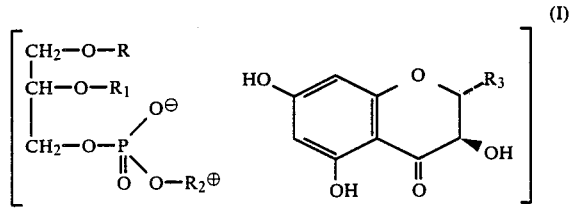

where R and $R_1$, which may be the same or different, each represent the acyl radical of palmitic or stearic or oleic or linoleic or linolenic acid; $R_2^\oplus$ represents one of the radicals: $-CH_2-CH_2-N^\oplus(CH_3)_3$, $-CH_2CH_2-N^\oplus H_3$, $-CH_2CH(COOH)-N^\oplus H_3$; and $R_3$ represents one of the radicals a, b or c:

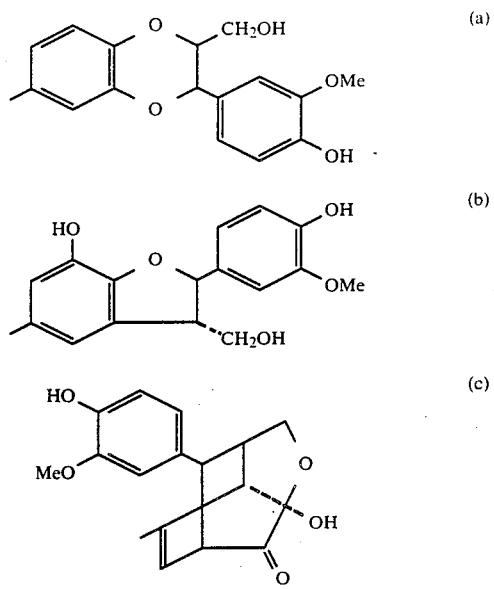

the molar ratio between flavanolignans and phospholipids being variable between 1:0.3 and 1:2.

The phospholipids used in the preparations can be natural or synthetic. Preferably use is made of natural phospholipids of vegetable origin (soy phospholipids) such as Lipoid S 100 ® (Lipoid KG-Ludwigshafen (West Germany)), having a minimum content of 90% phosphatidylcholine, containing on average 63% linoleic acid, 16% palmitic acid, 3.5% stearic acid and 11% oleic acid out of the total fatty acids; or natural phospholipids extracted from liver.

The complexes according to the invention have a marked lipophilic character and unexpectedly improve the oral absorption of complexed flavanolignan, and consequently show improved specific activity in the various pharmacological tests made by experimental methods already described in the literature with regard to the basic compounds.

According to the invention, the novel complexes are prepared by reacting from 0.3 moles to 2 moles, but preferably 1 mole, of a natural or synthetic phospholipid, which can be phosphatidylcholine, phosphatidylethanolamine or phosphatidylserine, with one mole of silybin, silidianin or silicristine, either alone or in the natural mixture (silymarin), in aprotic organic solvents such as dioxane or acetone, from which the complex can be isolated by precipitation with non-solvents such as aliphatic hydrocarbons or by lyophilization or by spray-drying.

The known described methods of obtaining liposomal drug complexes operate in the presence of water or a buffer solution. By contrast, the invention operates only with solvents having a reduced dielectric constant. Whereas the starting molecules (silybin, silidianin, etc.) are insoluble in chloroform, ethyl ether or benzene, they become extremely soluble in these solvents after forming a complex with the phospholipid. This change in chemical and physical properties is due to the formation of a true stable complex, as is clear from the modifications in the IR $^1$H-NMR and $^{13}$C-NMR spectra of the components after complexation.

The spectroscopic characteristics of the complex are appreciably different from those of the individual constituents taken separately and suggest a profound interaction between flavanolignan and the polar ends of the phospholipid. For example, the IR spectrum of phosphatidylcholine (particularly dipalmitoyl-phosphatidylcholine) at 1250 cm$^{-1}$ shows a band due to the group $P=O$; this band disappears in the spectrum of the 1:1 complex with silybin whereas it is present in a mechanical mixture of the two components.

The formation of the complex is also shown in the NMR spectra and in the relaxation times of the hydrogen and carbon atoms involved in the formation of bonds between the complex-forming agents. More particularly, the proton spectrum shows a substantial widening of the signals from hydroxyl protons, aromatic protons and the methoxy group of the flavanolignanes and the NMe$_3$ group of the lipid. On the other hand the $^1$H-NMR spectrum of a non-complexed mixture of phosphatidylcholine and silybin is the simple resultant of the spectra of the two components taken separately.

In the spectrum of $^{13}$C, the relaxation time of the nuclei most closely involved in the formation of the complex is sufficiently reduced to result in the disappearance of all the signals from flavanolignane and the choline radical and the glycerine radical of the phospholipid.

It is therefore assumed, without the scope of the invention being in any way linked to this interpretation, that silybin becomes bonded to the phospholipid via the polar end therreof, so as strongly to inhibit internal or intramolecular rotation. On the other hand the non-polar portion of the lipid, which is not involved in the formation of bonds, will be free to move, so that the complex becomes strongly liposoluble.

Silidianine and silicristine have physical and chemical properties similar to those of silybin; the same applies to silymarin, which contains the three active principles mixed together. Of course, the previously-mentioned chemical and physical considerations apply, though with some quantitiative differences, also to flavanolig-name-phospholipid complexes with a molar ratio different from 1:1.

As already mentioned, from the biological aspect these flavanolignan-phospholipid complexes unexpectedly have increased bioavailability per os, thus overcoming the known problems of absorption common to many phenolic substances and particularly to silymarin. Consequently the pharmacological activity of the novel compounds is more evident and demonstrable even when orally administered.

As shown in Table 1 (relating to silybin and its 1:1 complex with phosphatidylcholine from soy phospholipids), absorption in the rat is markedly in favour of the complexed form. The other constituents of silymarin behave similarly to silybin when administered in complex form.

Table 2 shows the activity of the same 1:1 complex of silybin with phosphatidylcholine from soy phospholipids in the conventional test of liver poisoning with carbon tetrachloride. The complex, when applied orally, results in a significant reduction in glutamic-oxalacetic transaminase (GOT) and glutamic-pyruvic transaminase (GPT) whereas equimolecular doses of silybin induce only a slight reduction in these enzymes. Similar results are shown in Table 3, concerning the 1:1 complex of silymarin with phosphatidylcholine from soy phospholipids.

There is also a very significant pharmacokinetic comparison in man, made after oral administration of equimolar doses of silybin and of its 1:1 complex with phosphatidylcholine from soy phospholipids; see Table 4.

TABLE 1

Pharmacokinetic comparison between equimolar doses of silybin and 1:1 silybin-phosphatidylcholine complex in the rat, after oral administration.

| Treatment | Dose mg/kg os | animals | Sampling times (hours) mcg/ml | | | | | | | |
|---|---|---|---|---|---|---|---|---|---|---|
| | | | 0.25 h | 0.50 h | 1.00 h | 2.00 h | 3.00 h | 4.00 h | 6.00 h | 8.00 h |
| Complex | 520* | 4 | 4.12 ± 1.59 | 3.69 ± 0.55 | 4.60 ± 0.87 | 2.00 ± 0.09 | 0.38 ± 0.09 | 0.11 ± 0.02 | 0.05 ± 0.00 | 0.00 ± 0.00 |
| Silybin | 200 | 4 | 0.07 ± 0.01 | 0.06 ± 0.01 | 0.11 ± 0.02 | 0.05 ± 0.00 | 0.05 ± 0.00 | 0.00 ± — | 0.00 ± — | — |

*Equivalent to 200 mg/kg silybin
0.00 = Non-determinable since below the limit of 0.05 mcg/ml.

TABLE 2

Anti-hepatotoxic activity of silybin and of 1:1 silybin-phosphatidylcholine complex in the rat, after poisoning with carbon tetrachloride.

| Treatment | Dose os | No. of animals per group | GPT U/L | GOT U/L |
|---|---|---|---|---|
| Normal controls | — | 10 | 22.40°° ± 1.93 | 88.50°° ± 5.20 |
| Poisoned controls | — | 10 | 145.40 ± 31.43 | 339.40 ± 59.07 |
| Silybin | 25 | 10 | 94.30 ± 21.87 (−35.2%) | 252.60 ± 48.04 (−25.6%) |
| Silybin | 250 | 10 | 94.90 ± 31.64 (−34.8%) | 200.00● ± 33.01 (−41.1%) |
| Complex | 65.8* | 10 | 65.90 ± 20.49 (−54.7%) | 181.80 ± 52.65 (−46.4%) |
| Complex | 658** | 10 | 46.90°° ± 9.61 (−67.8%) | 148.10°° ± 16.96 (−56.4%) |

●P < .05
*Equivalent to 25 mg silybin
°°P < .01
**Equivalent to 250 mg silybin

TABLE 3

Anti-hepatotoxic activity of silymarin and of 1:1 silymarin-phosphatidylcholine complex in the rat, after poisoning with carbon tetrachloride.

| Treatment | Dose mg/kg os | No. of animals per group | GPT U/L | GOT U/L |
|---|---|---|---|---|
| Normal controls | — | 10 | 26.33** ± 2.26 | 105.44** ± 4.98 |
| Poisoned controls | — | 10 | 146.50 ± 45.10 | 358.50 ± 64.15 |
| Silymarin | 25 | 10 | 125.30 ± 32.20 (−14.5) | 290.15 ± 38.52 (−19.1) |
| Silymarin | 250 | 10 | 82.44 ± 21.90 | 190.70* ± 28.85 |

TABLE 3-continued

Anti-hepatotoxic activity of silymarin and of 1:1 silymarin-phosphatidylcholine complex in the rat, after poisoning with carbon tetrachloride.

| Treatment | Dose mg/kg os | No. of animals per group | GPT U/L | GOT U/L |
|---|---|---|---|---|
| Complex | 65[a] | 10 | 110.22 ± 18.75 (−43.7) (−24.8) | 247.50 ± 26.52 (−46.8) (−31.0) |
| Complex | 650[b] | 10 | 50.48* ± 8.52 (−55.0) | 201.38* ± 23.64 (−43.8) |

*$P < 0.05$
[a]equivalent to 25 mg silymarin
**$P < 0.01$
[b]equivalent to 250 mg silymarin.

TABLE 4

Pharmacokinetic comparison between equimolar doses of silybin and of 1:1 silybin: phosphatidylcholine complex in man.

| Treatment | Dose os | No. of patients | Sampling times (hours) ng/ml | | | | | | | |
|---|---|---|---|---|---|---|---|---|---|---|
| | | | 0.25 h | 0.50 h | 1.00 h | 2.00 h | 3.00 h | 4.00 h | 6.00 h | 8.00 h |
| Complex | 700 | 4 | 0.00 | 46 | 78 | 79 | 108 | 112 | 50 | 40 |
| Silybin | 270 | 4 | 0.00 | 0.00 | 0.00 | 0.00 | 0.00 | 0.00 | 0.00 | 0.00 |

0.00 = Below the sensitivity of the method (35 ng/ml).

The products according to the invention are suited for treatment of acute or chronic liver disease of toxic, metabolic and/or infective origin; degenerative liver disease; and preventive treatment against liver damage resulting from the use of drugs and/or luxury substance having an injurious effect on the liver. The substances can be used in conventional oral pharmaceutical forms such as pills, dragees, capsules or packets, and in liquid forms in suspension.

The proposed daily adult dose of the 1:1 silybin/soya phosphatidylcholine complex is 130–1300 mg, equal to 50–500 mg of silybin.

The following examples illustrate the invention without limiting it.

EXAMPLE 1

1:1 Silybin/dipalmitoyl-phosphatidylcholine complex
(I, with R=R$_1$=palmitoyl;
R$_2$⊕=—CH$_2$—CH$_2$—N⊕(CH$_3$)$_3$; R$_3$=(a))

4.82 g (0.010 moles) of silybin was dissolved in 150 ml boiling acetone and treated with 8.06 g (0.011 moles) of dipalmitoyl phosphatidylcholine. The resulting solution was refluxed for an hour and then concentrated in vacuo to a volume of 30 ml. The concentrated solution was poured with stirring into 350 ml of n-hexane and after standing at room temperature overnight, the solid precipitate was collected by filtration, washed with n-hexane and dried in vacuo at 40° C. The product was 11.6 g of complex (95% yield) in the form of a yellowish white powder.

$E_{1\%}$=175.8 at 288 nm (CH$_3$OH).

Analysis for C$_{65}$H$_{102}$NO$_{18}$P (MW=1216.48) calc. % C=64.18; H=8.45; N=1.15; P=2.55; found % C=63.97; H=8.47; N=1.11; P=2.51.

EXAMPLE 2

1:1 Silicristin/dipalmitoyl-phosphatidylethanolamine complex (I, with R=R$_1$=palmitoyl;
R$_2$⊕=—CH$_2$—CH$_2$—N⊕H$_3$; R$_3$=(b))

A suspension of 4.82 g (0.010 moles) of silicristin in 100 ml dioxane was treated at room temperature and with stirring, with a solution containing 6.91 g (0.010 moles) of dipalmitoyl phosphatidylethanolamine in 200 ml dioxane.

The mixture was left to react for 5 hours and freeze-dried. The product was 11.7 g of complex in the form of a yellowish white powder.

$E_{1\%}$174.6 at 288 nm (CH$_3$OH).

Analysis for C$_{62}$H$_{96}$NO$_{18}$P (MW=1174.40) calc. % C=63.41; H=8.24; N=1.19; P=2.63; found % C=63.27; H=8.26; N=1.17; P=2.59.

EXAMPLE 3

1:1 Silydianin/distearoyl-phosphatidylcholine complex
(I, with R=R$_1$=stearoyl;
R$_2$⊕=—CH$_2$—CH$_2$—N⊕(CH$_3$)$_3$; R$_3$=(c))

A suspension of 4.82 g (0.010 moles) of silidianin in 150 ml acetone was refluxed with stirring with 8.68 g (0.011 moles) of distearoyl phosphatidylcholine for about an hour. The reaction mixture was concentrated in vacuo to a volume of 35 ml and diluted with 400 ml n-hexane. After standing overnight at room temperature, the solid precipitate was collected by filtration, washed with n-hexane and dried at 40° C. in vacuo. The product was 11.1 g of a yellowish white compled (87.4% yield).

$E_{1\%}$=148.8 at 288 mn (CH$_3$OH).

Analysis for C$_{69}$H$_{110}$NO$_{18}$P (MW=1272.59) calc. % C=65.12; H=8.71; N=1.10; P=2.43; found % C=64.98; H=8.73; N=1.12; P=2.48.

EXAMPLE 4

1:1 Silybin/soy phosphatidylcholine complex

A suspension of 4.82 g silybin (0.010 moles) in 150 ml acetone was treated at room temperature with stirring with 9.2 g (0.012 moles) of "Lipoid S 100 ®" (average molecular weight 770). The reaction mixture became clear after about 3 hours and was concentrated in vacuo to a volume of 30 ml. After being diluted with 300 ml n-hexane the complex was precipitated and was collected by filtration after one night and dried in vacuo at 40° C. The yield was 11.9 g (94%) of product in the form of a yellowish white powder.

$E_{1\%}$=172.8 at 288 nm (CH$_3$OH).

Analysis: (MW=1252) calc. % N=1.12; P=2.48; found % N=1.15; P=2.55.

EXAMPLE 5

1:1 Silymarin/soy phosphatidylcholine complex

A solution of 5 g silymarin in 100 ml acetone was treated with stirring at room temperature, with 8 g of "Lipoid S 100®". After complete solubilization the reaction mixture was concentrated in vacuo to 30 ml and poured with stirring into 300 ml ligroin. The precipitate, which was left to settle overnight, was collected by filtration, washed with ligroin and dried in vacuo at 40° C. The product was 11.1 g of complex.

$E_{1\%} = 170.2$ at 288 nm (CH$_3$OH).
Analysis: found % N=1.12; P=2.50.

EXAMPLE 6

1:2 Silybin/soy phosphatidylcholine complex

A suspension of 4.82 g silybin (0.010 moles) in 75 ml dioxane was treated with stirring, with a solution containing 15.4 g (0.020 moles) of "Lipoid S 100 ®". The reaction mixture became clear after 4 hours and was freeze-dried, giving 20 g of pale yellow complex.

$E_{1\%} = 160$ at 288 nm (CH$_3$OH).

Analysis: (MW=2022) calc. % N=1.38; P=3.07; found % N=1.35; P=3.11.

EXAMPLE 7

1:0.3 Silybin/soy phosphatidylcholine complex

A solution containing 2.41 g (0.005 moles) of silybin and 100 ml dioxane was treated at 60° C. with 0.770 g (0.001 moles) of "Lipoid S 100 ®" for an hour. The reaction mixture was evaporated to dryness in vacuo and the residue was dissolved in 100 ml chloroform.

The non-complexed silibyn present at the bottom was eliminated by filtration and the mother-liquors containing the complex were evaporated to dryness in vacuo.

The residue, dried at 30° C. in vacuo, comprised 2.3 g of the complex in the form of a yellowish white powder.

$E_{1\%} = 300$ at 288 nm (CH$_3$OH).

Analysis: (MW=713) calc. % N=0.59; P=1.30; found % N=0.56; P=1.34.

EXAMPLE 8

Pills containing silybin/soy phosphatidylcholine complex

Each 1.2 g pill contained:
Complex (equal to 200 mg silybin): 520 mg
Granular cellulose: 390 mg
Lactose: 100 mg
Starch: 100 mg
PVP: 10 mg
Carboxymethyl starch: 60 mg
Magnesium stearate: 20 mg.

EXAMPLE 9

Capsules containing 1:1 silybin/soy phosphatidylcholine complex

Each 0.275 g capsule contained:
Complex (equal to 100 mg silybin): 260 mg
Silica powder: 10 mg
PVP: 2.5 mg
Magnesium stearate: 2.5 mg.

EXAMPLE 10

Granulate for suspension in water, containing 1:1 silybin/soy phosphatidylcholine complex Each 3 g packet contained:
Complex (equal to 200 mg silybin): 520 mg
Lactose: 2000 mg
Mannitol: 238 mg
Ammonium glycyrrhizinate: 10 mg
Sodium saccharine: 2 mg
Dried Orange Juice: 200 mg
Flavouring: 30 mg.

EXAMPLE 11

Capsules containing 1:1 silymarin/soy phosphatidylcholine complex

Each capsule was identical to the capsules of Example 9, but contained 260 mg of 1:1 silymarin/phosphatidylcholine complex (equal to 100 mg silymarin) instead of the complex with silybin.

EXAMPLE 12

Granulate for suspension in water, containing 1:1 silymarin/phosphatidylcholine complex Each 3 g packet was identical to the packet of Example 10, but contained 520 mg of 1:1 silymarin/phosphatidylcholine complex (equal to 200 mg silymarin) instead of the complex with silybin.

We claim:

1. A complex of one or more flavanolignans with one or more phospholipids having the formula I

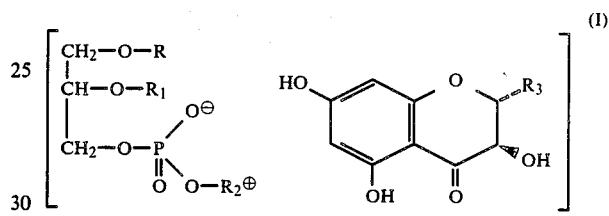

wherein R and R$_1$, are the same or different, and each is the acyl residue of palmitic, stearic, oleic, linoleic or linolenic acid; R$_2^\oplus$ is one of the residues $\oplus$—CH$_2$—CH$_2$—N$^\oplus$(CH$_3$)$_3$, —CH$_2$CH$_2$—N$^\oplus$H$_3$, or —CH$_2$CH(COOH)—N$^\oplus$H$_3$; and R$_3$ represents one of the radicals a, b or c:

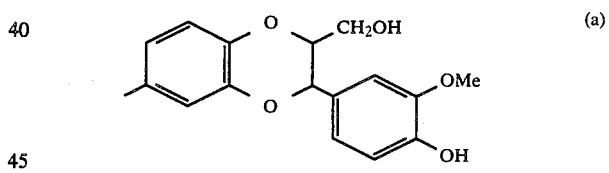

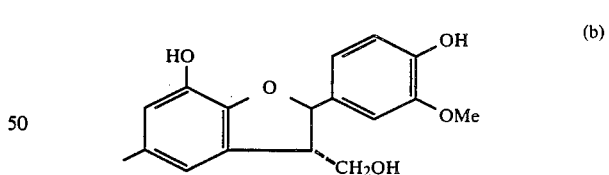

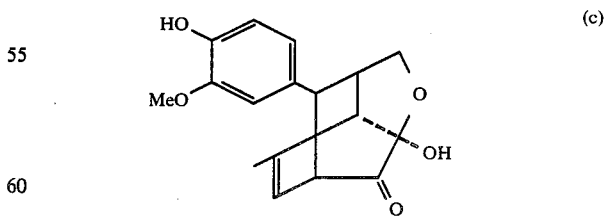

the molar ratio between the flavanolignan and phospholipids is between 1:0.3 and 1:2.

2. The complex of silybin with dipalmitoyl phosphatidylcholine according to claim 1.

3. The complex of silicristin with dipalmitoyl phosphatidylethanolamine according to claim 1.

4. The complex of silidianin with distearoyl phosphatidylcholine according to claim 1.

5. The complex according to claim 1 wherein the molar ratio of said flavanolignan to phospholipid is 1:1.

6. The complex of silymarin with soy phosphatidylcholine according to claim 1.

7. The complex according to claim 6 wherein the molar ratio of silymarin to soy phosphatidylcholine is between 1:0.3 and 1:2.

8. A pharmaceutical composition in unit dose for oral administration for treatment of acute or chronic liver disease of toxic, metabolic and/or infective origin or of degenerative nature, and for prevention of liver damage resulting from the use of drugus injurious to the liver, which consists of administering an effective amount of a complex of one or more flavanolignans with one or more phospholipids having the formula I

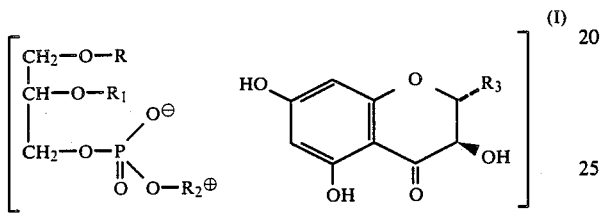

wherein R and $R_1$, are the same or different, and each is the acyl residue of palmitic, stearic, oleic, linoleic or linolenic acid; $R_2^\oplus$ is one of the residues $^\oplus$—$CH_2$—$CH_2$—$N^\oplus(CH_3)_3$, —$CH_2CH_2$—$N^\oplus H_3$, or —$CH_2CH(COOH)$—$N^\oplus H_3$; and $R_3$ represents one of the radicals a, b or c:

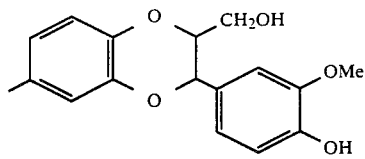

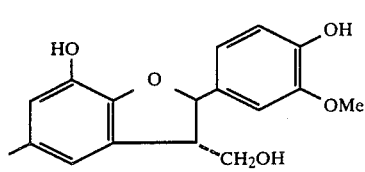

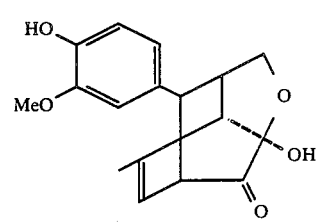

the molar ratio between the flavanolignan and phospholipids is between 1:0.3 and 1:2.

* * * * *